(12) United States Patent
Fairhurst

(10) Patent No.: US 8,076,489 B2
(45) Date of Patent: Dec. 13, 2011

(54) 5-HYDROXY-BENZOTHIAZOLE DERIVATIVES HAVING BETA-2-ADRENORECEPTOR AGONIST ACTIVITY

(75) Inventor: Robin A Fairhurst, Horsham (GB)

(73) Assignee: Novartis AG, Basel (CH)

( * ) Notice: Subject to any disclaimer, the term of this patent is extended or adjusted under 35 U.S.C. 154(b) by 29 days.

(21) Appl. No.: 11/718,829

(22) PCT Filed: Nov. 28, 2005

(86) PCT No.: PCT/EP2005/012686
§ 371 (c)(1),
(2), (4) Date: May 8, 2007

(87) PCT Pub. No.: WO2006/056471
PCT Pub. Date: Jun. 1, 2006

(65) Prior Publication Data
US 2008/0096940 A1    Apr. 24, 2008

(30) Foreign Application Priority Data
Nov. 29, 2004    (GB) ................... 0426164.0

(51) Int. Cl.
*A61K 31/428*    (2006.01)
*C07D 277/68*    (2006.01)
(52) U.S. Cl. ...................... 548/165; 514/367
(58) Field of Classification Search ............. 548/165
See application file for complete search history.

(56) References Cited

U.S. PATENT DOCUMENTS

| | | | |
|---|---|---|---|
| 4,091,218 A | 5/1978 | Advani | |
| 4,119,412 A | 10/1978 | Advani | |
| 5,648,370 A * | 7/1997 | Bonnert et al. | 514/367 |
| 6,670,376 B1 | 12/2003 | Moran et al. | |
| 2004/0167167 A1 | 8/2004 | Mammen et al. | |
| 2004/0224982 A1 | 11/2004 | Axt et al. | |
| 2005/0182092 A1 | 8/2005 | Chao et al. | |
| 2006/0035933 A1 | 2/2006 | Mammen et al. | |
| 2006/0106075 A1 | 5/2006 | Cuenoud et al. | |
| 2007/0249586 A1 | 10/2007 | Cuenoud et al. | |
| 2009/0264459 A1 | 10/2009 | Collingwood et al. | |

FOREIGN PATENT DOCUMENTS

| | | | |
|---|---|---|---|
| CA | 2493765 A1 * | 2/2004 | |
| CA | 2 565 243 A1 | 11/2005 | |
| CN | 1085899 A | 4/1994 | |
| JP | 52-83383 A | 7/1977 | |
| WO | WO 95/02585 A1 | 1/1995 | |
| WO | WO 97/10227 A1 | 3/1997 | |
| WO | WO 99/09018 A1 | 2/1999 | |
| WO | WO-99/09018 A1 * | 2/1999 | |
| WO | WO 99/36095 A1 | 7/1999 | |
| WO | WO 2004/016601 | 2/2004 | |
| WO | WO 2004/087142 A1 | 10/2004 | |
| WO | WO 2004/106333 A1 | 12/2004 | |
| WO | WO 2005/110990 A1 | 11/2005 | |

OTHER PUBLICATIONS

Barnes et al., European Respiratory Journal (2005), 25(6), pp. 1084-1106.*
Souillac, et al., Characterization of Delivery Systems, Differential Scanning Calorimetry in Encyclopedia of Controlled Drug Delivery, 1999, John Wiley & Sons, pp. 212-227.*
Vippagunta et al., Advanced Drug Delivery Reviews, 48 (2001), pp. 3-26.*
An English translation of WO 99/09018, 1999.*
R. T. Brittain et al., "Sympathomimetic Bronchodilator Drugs", Pharmac. Ther. B., vol. 2 (1976), pp. 423-462.
Jack, "A way of looking at agonism and antagonism: Lessons from salbutamol, salmeterol and other β-adrenoceptor agonists", Br. J. clin. Pharmac., vol. 31 (1991), pp. 501-514.
Suzuki et al., "S1319: A Novel β$_2$-adrenoceptor Agonist from a Marine Sponge *Dysidea* SP.", Bioorganic & Medicinal Chemistry Letters, vol. 9, No. 10 (1999), pp. 1361-1364.
Suzuki et al., "Tracheal relaxing effects and β$_2$ adrenoceptor selectivity of S1319, a novel sponge-derived bronchodilator agent, in isolated guinea-pig tissues", British Journal of Pharmacology, vol. 128 (1999), pp. 716-720.
Suzuki et al., "The effects of S1319, a novel marine sponge-derived β$_2$-adrenoceptor agonist, on IgE-mediated activation of human cultured mast cells", Inflamm. Res., vol. 49 (2000), pp. 86-94.
Bernard Cuenoud; U.S. PTO Office Action, U.S. Appl. No. 11/823,622, Mar. 28, 2008, 13 pgs.
Bernard Cuenoud; U.S. PTO Office Action, U.S. Appl. No. 10/522,359, Jan. 9, 2007, 19 pgs.
Database WPI, Section Ch, Week 199915, Derwent Publications Ltd., London, GB, AN 1999-180948 (1999), 2 pgs.
Bernard Cuenoud; U.S. PTO Office Action, U.S. Appl. No. 11/823,622, May 14, 2010, 20 pgs.

(Continued)

*Primary Examiner* — Laura L. Stockton
(74) *Attorney, Agent, or Firm* — Paul D. Strain; Strain & Strain PLLC

(57) ABSTRACT

Compounds of formula (I) in free or salt or solvate form, wherein T has the meaning as indicated in the specification, are useful for treating conditions that are prevented or alleviated by activation of the β$_2$-adrenoreceptor. Pharmaceutical compositions that contain the compounds and a process for preparing the compounds are also described.

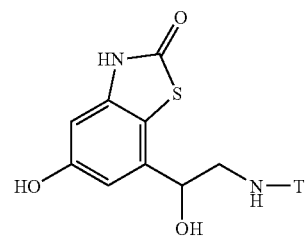

I

12 Claims, No Drawings

OTHER PUBLICATIONS

Cuenoud; U.S. PTO Office Action, U.S. Appl. No. 11/823,622, Nov. 12, 2010, 27 pgs.

Cuenoud; U.S. PTO Advisory Action, U.S. Appl. No. 11/823,622, Feb. 18, 2011, 4 pgs.

Collingwood, U.S. PTO Restriction Requirement, U.S. Appl. No. 12/308,231, Mar. 23, 2011, 8 pgs.

* cited by examiner

5-HYDROXY-BENZOTHIAZOLE DERIVATIVES HAVING BETA-2-ADRENORECEPTOR AGONIST ACTIVITY

This invention relates to organic compounds, their preparation and use as pharmaceuticals.

The invention provides in one aspect a compound of formula I

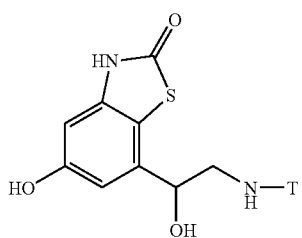

in free or salt or solvate form, where

T is hydrogen or $C_1$-$C_{10}$-alkyl optionally substituted at one, two or three positions by $C_1$-$C_{10}$-alkoxy, —$NR^1R^2$, a 5- or 6-membered heterocyclic ring containing at least one ring heteroatom selected from the group consisting of nitrogen, oxygen and sulphur, or by a $C_3$-$C_{15}$-carbocyclic group, said $C_3$-$C_{15}$-carbocyclic group being optionally substituted at one, two or three positions by halo, $C_1$-$C_{10}$-alkyl, $C_3$-$C_{10}$-cycloalkyl, halo-$C_1$-$C_{10}$-alkyl, —$NR^3R^4$, a 5- or 6-membered heterocyclic ring containing at least one ring heteroatom selected from the group consisting of nitrogen, oxygen and sulphur, or by $C_1$-$C_{10}$-alkoxy optionally substituted at one, two or three positions by $C_6$-$C_{10}$-aryl;

or T is a $C_3$-$C_{15}$-carbocyclic group optionally substituted at one, two or three positions by halo, $C_1$-$C_{10}$-alkyl, $C_3$-$C_{10}$-cycloalkyl, halo-$C_1$-$C_{10}$-alkyl, —$NR^5R^6$, a 5- or 6-membered heterocyclic ring containing at least one ring heteroatom selected from the group consisting of nitrogen, oxygen and sulphur, or by $C_1$-$C_{10}$-alkoxy optionally substituted at one, two or three positions by $C_1$-$C_4$-alkyl or $C_6$-$C_{10}$-aryl; and $R^1$, $R^2$, $R^3$, $R^4$, $R^5$ and $R^6$ are independently hydrogen, $C_1$-$C_{10}$-alkyl, $C_1$-$C_{10}$-alkoxy, $C_3$-$C_{10}$-cycloalkyl or $C_6$-$C_{10}$-aryl.

Terms used in this specification have the following meanings:

"Optionally substituted at one, two or three positions" as used herein means the group referred to can be substituted at one, two or three positions by any one or any combination of the radicals listed thereafter.

"Halo" or "halogen" as used herein denotes a element belonging to group 17 (formerly group VII) of the Periodic Table of Elements, which may be, for example, fluorine, chlorine, bromine or iodine. Preferably halo or halogen is chloro.

"$C_1$-$C_{10}$-alkyl" as used herein denotes straight chain or branched alkyl having 1 to 10 carbon atoms. When T is $C_1$-$C_{10}$-alkyl it is preferably $C_1$-$C_8$-alkyl especially n-propyl, isopropyl, n-butyl, s-butyl, —$C(CH_3)_2C_2H_5$, —$CH(CH_3)C_3H_7$ or —$CH(CH_3)CH_2C(CH_3)_3$. When T is a $C_5$-$C_{10}$-carbocyclic group substituted at one, two or three positions by $C_1$-$C_8$-alkyl, that $C_1$-$C_{10}$-alkyl is preferably $C_1$-$C_4$-alkyl, especially ethyl or s-butyl. When any one of $R^1$, $R^2$, $R^3$, $R^4$, $R^5$ and $R^6$ is $C_1$-$C_{10}$-alkyl, it is preferably $C_1$-$C_4$-alkyl, especially methyl.

"$C_1$-$C_{10}$-alkoxy" as used herein denotes straight chain or branched alkoxy having 1 to 10 carbon atoms. When T is $C_1$-$C_{10}$-alkyl substituted at one, two or three positions by a $C_5$-$C_{15}$-carbocyclic group that is substituted at one, two or three positions by $C_1$-$C_{10}$-alkoxy, that $C_1$-$C_{10}$-alkoxy is preferably $C_1$-$C_4$-alkoxy, especially methoxy or n-butoxy. When T is a $C_5$-$C_{15}$-carbocyclic group substituted at one, two or three positions by $C_1$-$C_{10}$-alkoxy, that $C_1$-$C_{10}$-alkoxy is preferably $C_1$-$C_4$-alkoxy, especially ethoxy. When any one of $R^1$, $R^2$, $R^3$, $R^4$, $R^5$ and $R^6$ is $C_1$-$C_{10}$-alkoxy, it is preferably $C_1$-$C_4$-alkoxy.

"$C_3$-$C_{10}$-cycloalkyl" as used herein denotes cycloalkyl having 3 to 10 ring carbon atoms, for example a monocyclic group such as a cyclopropyl, cyclobutyl, cyclopentyl, cyclohexyl, cycloheptyl, cyclooctyl, cyclononyl or cyclodecyl, or a bicyclic group such as bicycloheptyl or bicyclooctyl. Preferably $C_3$-$C_{10}$-cycloalkyl is $C_3$-$C_6$-cycloalkyl, especially cyclopentyl or cyclohexyl.

"Halo-$C_1$-$C_{10}$-alkyl" as used herein denotes $C_1$-$C_{10}$-alkyl as hereinbefore defined substituted by one or more halogen atoms, preferably one, two or three halogen atoms. Preferably halo-$C_1$-$C_{10}$-alkyl is fluoro-$C_1$-$C_4$-alkyl.

"$C_6$-$C_{10}$-aryl" as used herein denotes a monovalent carbocyclic aromatic group that contains 6 to 10 carbon atoms and which may be, for example, a monocyclic group such as phenyl or a bicyclic group such as naphthyl. Preferably $C_6$-$C_{10}$-aryl is $C_6$-$C_8$-aryl, especially phenyl. "$C_3$-$C_{15}$-carbocyclic group" as used herein denotes a carbocyclic group having 3 to 15 ring carbon atoms, for example a monocyclic group, either aromatic or non-aromatic, such as a cyclopropyl, cyclobutyl, cyclopentyl, cyclohexyl, cycloheptyl, cyclooctyl or phenyl, or a bicyclic group such as bicyclooctyl, bicyclononyl, bicyclodecyl, indanyl or indenyl. When T is $C_1$-$C_{10}$-alkyl substituted at one, two or three positions by a $C_5$-$C_{15}$-carbocyclic group, that $C_5$-$C_{15}$-carbocyclic group is preferably a $C_5$-$C_{10}$-carbocyclic group, especially a monocyclic group such as phenyl or cyclohexyl. When T is a $C_5$-$C_{15}$-carbocyclic group, it is preferably a $C_5$-$C_{10}$-carbocyclic group, especially a monocyclic non-aromatic group such as cyclopentyl or a bicyclic group such as indanyl.

"5- or 6-membered heterocyclic ring containing at least one ring heteroatom selected from the group consisting of nitrogen, oxygen and sulphur" as used herein may be, for example, pyrrole, pyrrolidine, pyrazole, imidazole, triazole, tetrazole, furan, thiadiazole, isothiazole, thiophene, oxadiazole, pyridine, oxazole, isoxazole, pyrazine, pyridazine, pyrimidine, piperazine, morpholino, triazine, oxazine or thiazole. Preferred 5- or 6-membered heterocyclic rings include unsaturated rings such as pyridine, furan and thiophene.

"Solvate" as used herein denotes a molecular complex comprising a compound of the present invention and one or more pharmaceutically acceptable solvent molecules, for example ethanol. The term "hydrate" is used when the solvent is water.

Throughout this specification and in the claims that follow, unless the context requires otherwise, the word "comprise", or variations such as "comprises" or "comprising", will be understood to imply the inclusion of a stated integer or step or group of integers or steps but not the exclusion of any other integer or step or group of integers or steps.

Preferred compounds of the present invention include compounds of formula I, in free or salt or solvate form, where T is $C_1$-$C_{10}$-alkyl optionally substituted at one, two or three positions by —$NR^1R^2$ or a $C_5$-$C_{15}$-carbocyclic group, said $C_5$-$C_{15}$-carbocyclic group being optionally substituted at one, two or three positions by halo, —$NR^3R^4$ or $C_1$-$C_{10}$-alkoxy;

or T is a $C_5$-$C_{15}$-carbocyclic group optionally substituted at one, two or three positions by $C_1$-$C_{10}$-alkyl, $C_3$-$C_{10}$-cycloalkyl, —$NR^5R^6$ or by $C_1$-$C_{10}$-alkoxy optionally substituted at one, two or three positions by $C_6$-$C_{10}$-aryl; and $R^1$, $R^2$, $R^3$, $R^4$, $R^5$ and $R^6$ are independently $C_1$-$C_{10}$-alkyl or $C_6$-$C_{10}$-aryl.

Especially preferred compounds of the present invention include compounds of formula I where T is $C_1$-$C_{15}$-alkyl optionally substituted at one position by —$NR^1R^2$ or a $C_5$-$C_{10}$-carbocyclic group, said $C_5$-$C_{10}$-carbocyclic group being optionally substituted at one or two positions by halo, —$NR^3R^4$ or $C_1$-$C_4$-alkoxy;

or T is a $C_5$-$C_{10}$-carbocyclic group optionally substituted at one or two positions by $C_1$-$C_8$-alkyl, $C_3$-$C_{10}$-cycloalkyl, —$NR^5R^6$ or by $C_1$-$C_4$-alkoxy optionally substituted at one position by $C_6$-$C_8$-aryl, especially phenyl; and $R^1$, $R^2$, $R^3$, $R^4$, $R^5$ and $R^6$ are independently $C_1$-$C_4$-alkyl or $C_6$-$C_8$-aryl, especially phenyl.

The compounds represented by formula I are capable of forming acid addition salts, particularly pharmaceutically acceptable acid addition salts. Pharmaceutically acceptable acid addition salts of the compound of formula I include those of inorganic acids, for example, hydrohalic acids such as hydrofluoric acid, hydrochloric acid, hydrobromic acid or hydroiodic acid, nitric acid, sulfuric acid, phosphoric acid; and organic acids, for example aliphatic monocarboxylic acids such as formic acid, acetic acid, trifluoroacetic acid, propionic acid and butyric acid, aliphatic hydroxy acids such as lactic acid, citric acid, tartaric acid or malic acid, dicarboxylic acids such as maleic acid or succinic acid, aromatic carboxylic acids such as benzoic acid, p-chlorobenzoic acid, diphenylacetic acid, para-biphenyl benzoic acid or triphenylacetic acid, aromatic hydroxy acids such as o-hydroxybenzoic acid, p-hydroxybenzoic acid, 1-hydroxynaphthalene-2-carboxylic acid or 3-hydroxynaphthalene-2-carboxylic acid, cinnamic acids such as 3-(2-naphthalenyl)propenoic acid, para-methoxy cinnamic acid or para-methyl cinnamic acid, and sulfonic acids such as methanesulfonic acid or benzenesulfonic acid. These salts may be prepared from compounds of formula I by known salt-forming procedures.

The compounds represented by formula I may exist in unsolvated or solvate forms. Pharmaceutically acceptable solvates include hydrates and solvates wherein the solvent of crystallisation may be isotopically substituted, for example $D_2O$, $d_6$-acetone or $d_6$-DMSO.

The compounds represented by formula I include at least one asymmetric carbon atom and thus they exist in individual optically active isomeric forms or as mixtures thereof, e.g. as racemic or diastereomeric mixtures. The present invention embraces individual optically active R and S isomers as well as mixtures, e.g. racemic or diastereomeric mixtures, thereof. These isomers may be separated by conventional techniques, e.g. by fractional crystallization or column chromatography.

Specific especially preferred compounds of the invention are those described hereinafter in the Examples.

The present invention also provides a process for the preparation of compounds of formula I in free or salt or solvate form. They can be prepared by a process comprising:

(i) (A) reacting a compound of formula II

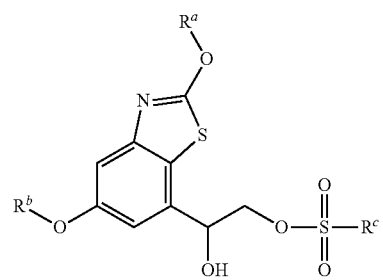

where $R^a$ and $R^b$ are protecting groups and $R^c$ is $C_1$-$C_4$-alkyl or $C_6$-$C_{10}$-aryl, with a compound of formula III $H_2N$-T    III where T is as hereinbefore defined; or
(B) reacting a compound of formula IIA

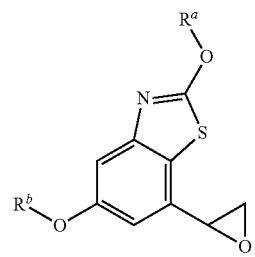

where $R^a$ and $R^b$ are protecting groups, with a compound of formula III, where T is as hereinbefore defined;
(ii) removing the protecting groups; and
(iii) recovering the resultant compound of formula I in free or salt or solvate form.

Process variant A may be carried out using known procedures for reacting sulfonic acid esters with amines or analogously as hereinafter described in the Examples. $R^c$ is preferably $C_1$-$C_4$-alkyl, but especially methyl. The reaction is conveniently carried out in an organic solvent such as toluene. The reaction temperature is conveniently from 0° C. to 200° C., preferably from 70° C. to 100° C., especially from 80° C. to 90° C. The temperature may be achieved by conventional heating or by microwave irradiation.

Process variant B may be carried out using known procedures for reacting epoxides with amines or analogously as hereinafter described in the Examples. The reaction is conveniently carried out in an organic solvent such as toluene. The reaction temperature is conveniently from 0° C. to 200° C., preferably from 70° C. to 100° C., especially from 80° C. to 90° C. The temperature may be achieved by conventional heating or by microwave irradiation.

The protecting groups, $R^a$ and $R^b$, may be chosen in accordance with the nature of the functional group, for example as described in *Protective Groups in Organic Synthesis*, T. W. Greene and P. G. M. Wuts, John Wiley & Sons Inc, Third Edition, 1999, which reference also describes procedures suitable for replacement of the protecting groups by hydrogen. $R^a$ is preferably $C_1$-$C_4$-alkyl, especially isopropyl. $R^b$ is preferably $C_1$-$C_4$-alkyl, especially tert-butyl.

The protecting group may be introduced and removed using any conventional procedure. For example, when a hydroxy group is protected by a benzyl group, the latter may be removed by catalytic hydrogenation in the presence of palladium on charcoal using conventional procedures, such as those used hereinafter in the Examples.

Compounds of formula I in free form may be converted into salt form, and vice versa, in a conventional manner. The compounds in free or salt form can be obtained in the form of hydrates or solvates containing a solvent used for crystallisation. Compounds of formula I can be recovered from reaction mixtures and purified in a conventional manner. Isomers, such as enantiomers, may be obtained in a conventional manner, e.g. by fractional crystallisation or asymmetric synthesis from correspondingly asymmetrically substituted, e.g. optically active, starting materials.

Compounds of formula II are novel and can be prepared by reacting a compound of formula IV

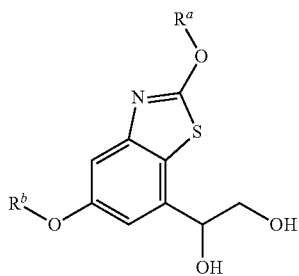

IV where $R^a$ and $R^b$ are protecting groups, with a sulfonylchloride, for example methane sulphonyl chloride using known procedures for selective mono-sulphonylation reactions as described Zhou et al *J. Organic Letters* (2002), 4(1), pages 43-46 or analogously as hereinafter described in the Examples. Reaction with (R)-1-(5-tert-Butoxy-2-isopropoxy-benzothiazol-7-yl)-ethane-1,2-diol gives the R-enantiomer whereas reaction with (S)-1-(5-tert-Butoxy-2-isopropoxy-benzothiazol-7-yl)-ethane-1,2-diol gives the S-enantiomer. The reaction is conveniently carried out in an organic solvent such as pyridine. The reaction temperature is conveniently from −20° C. to 30° C., but preferably about 0° C.

Compounds of formula IIA are novel and may be prepared using known methods for preparing oxiranyl-substituted heterocyclic compounds, for example as described in international patent application WO 04/016601. For example, compounds of formula IIA may prepared by heating compounds of formula II, e.g. between room temperature and 150° C., but preferably between 50 and 100° C., in the presence of a base in solvent such as toluene, tetrahydrofuran or dichloroethane. Compounds of formula IIA may also be formed as intermediates during the aforementioned reaction of compounds of formula II with compounds of formula III to form compounds of formula I.

Compounds of formula III are known or may be prepared using procedures that are known or are analogous to those hereinafter described in the Examples.

Compounds of formula IV may be prepared by reacting a compound of formula V

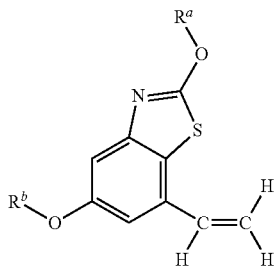

V where $R^a$ and $R^b$ are protecting groups, with a dihydroxylating agent such as osmium tetroxide, either in the presence or absence a catalyst, for example (DHQD)2PHAL (1,4-bis(dihydroquinidinyl)phthalazine) and re-oxidant, for example $K_3Fe(CN)_6$, or with premixed dihydroxylating reagents such as AD-mix-α or AD-mix-β using known procedures for assymetrically dihydroxylating alkenes or analogously as hereinafter described in the Examples. The reaction is conveniently carried out in an organic solvent, for example tert-butanol/water, with osmium tetroxide, preferably in the presence of a catalyst such as $(DHQD)_2PHAL$ and with $K_3Fe(CN)_6$ as the reoxidant. The reaction temperature is conveniently from −10° C. to 10° C., but preferably about 0° C.

Compounds of formula V may be prepared by olefination of a compound of formula VI

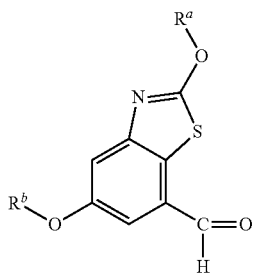

VI where $R^a$ and $R^b$ is a protecting group, using known procedures for the reaction of aldehydes to form alkenes, for example the Wittig reaction, or analogously as hereinafter described in the Examples. The reaction is conveniently carried out in an organic solvent, for example THF or DCM. The reaction temperature is conveniently from 10° C. to 40° C., but preferably room temperature.

Compounds of formula VI may be prepared by reacting a compound of formula VII

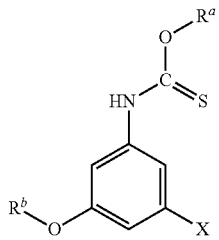

VII where $R^a$ and $R^b$ are protecting groups and X is halo, preferably fluoro, with a strong base, for example tert.butyl lithium, and the intermediate anion quenched by the addition of an electrophile, for example dimethylformamide, using the procedure described by Stanetty et al *J. Org. Chem.* 1996, 61, 5130-5133, or analogously as hereinafter described in the Examples. The reaction is conveniently carried out in an organic solvent, for example THF. The reaction temperature is conveniently over a range of −90° C. to 20° C., but preferably between about −78° C. to about −10° C.

Compounds of formula VII may be prepared by reacting a compound of formula VIII

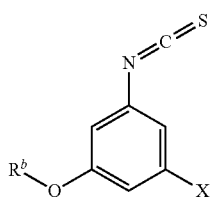

VIII where $R^b$ is a protecting group and X is halo, with a compound of formula IX

 IX where $R^a$ is a protecting group, using known procedures for reacting isothiocyantes with alcohols to form thiocarbamates or analogously as hereinafter described in the Examples. $R^1$ is preferably $C_1$-$C_4$-alkyl, especially isopropyl. The reaction is conveniently carried out preferably in the presence of a base, for example triethylamine. The reaction temperature is conveniently from 0° C. to 120° C., but preferably about 60° C.

Compounds of formula VIII may be prepared by known procedures for the conversion of anilines to isothiocyanates, for example by reacting a compound of formula X

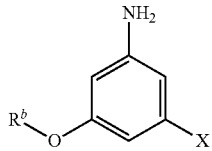 X where $R^b$ is a protecting group and X is halo, with thiophosgene (thiocarbonyl dichloride) using known procedures for converting amines to isothiocyanates or analogously as hereinafter described in the Examples. The reaction is conveniently carried out in an organic solvent such as chloroform, preferably in the present of a base, for example potassium carbonate. The reaction temperature is conveniently from −20° C. to 20° C., but preferably about 0° C.

Compounds of formulae IX are known or may be prepared using procedures that are known or are analogous to those hereinafter described in the Examples. Compounds of formula I in free, salt or solvate form are useful as pharmaceuticals. Accordingly the invention also provides a compound of formula I in free, salt or solvate form for use as a pharmaceutical. The compounds of formula I in free, salt or solvate form, hereinafter referred to alternatively as "agents of the invention", have good β2-adreno-receptor agonist activity. The $β_2$ agonist activity, onset of action and duration of action of the agents of the invention may be tested using the guinea pig tracheal strip in vitro assay according to the procedure of R. A. Coleman and A. T. Nials, *J. Pharmacol. Methods* 1989, 21, 71. The binding potency and selectivity for the β2-adrenoreceptor relative to the β1-adrenoreceptor can be measured by a classical filtration binding assay according to the procedure of *Current Protocols in Pharmacology* (S. J. Enna (editor-in-chief) et al, John Wiley & Son, Inc, 1998), or by cAMP determination in cells expressing $β_2$- or $β_1$-adreno-ceptor, according to the procedure of B. January et al, *Brit. J. Pharmacol.* 1998, 123, 701.

The agents of the invention commonly have a rapid onset of action and have a prolonged stimulating action on the $β_2$-adrenoreceptor, compounds of the Examples hereinbelow having $K_i$ ($β_2$) values of the order of 0.1 to 1000 nM, having durations of action of the order of 1 to greater than 12 hours. Many of the compounds have binding selectivities for the $β_2$-adrenoreceptor relative to the $β_1$-adrenoreceptor from 1.5 to 500. The compounds of Examples 2, 4, 9, 14 and 17 have $β_2$ binding potencies, measured by a classical filtration binding assay, represented by $K_i$ values of 0.061, 0.027, 0.016, 0.056 and 0.002 μM respectively.

The compounds of Examples 1 and 18 have T(50%) times (in minutes) of >672 at 100 nM concentration, and 595 at 10 nM concentration respectively in the guinea-pig tracheal strip assay, where T(50%) is the time for inhibition of contraction to decay to 50% of its maximum value.

Having regard to their $β_2$ agonist activity, the agents of the invention are suitable for use in the treatment of any condition which is prevented or alleviated by activation of the $β_2$-adrenoreceptor. In view of their long acting selective $β_2$ agonist activity, the agents of the invention are useful in the relaxation of bronchial smooth muscle and the relief of bronchoconstriction. Relief of bronchoconstriction can be measured in models such as the in vivo plethysmography models of Chong et al, *J. Pharmacol. Toxicol. Methods* 1998, 39, 163, Hammelmann et al, *Am. J. Respir. Crit. Care Med.,* 1997, 156, 766 and analogous models.

The agents of the invention are therefore useful in the treatment of obstructive or inflammatory airways diseases. In view of their long duration of action, it is possible to administer the agents of the invention once-a-day in the treatment of such diseases. In another aspect, agents of the invention commonly exhibit characteristics indicating a low incidence of side effects commonly encountered with $β_2$ agonists such as tachycardia, tremor and restlessness, such agents accordingly being suitable for use in on demand (rescue) treatment as well as prophylactic treatment of obstructive or inflammatory airways diseases.

Treatment of a disease in accordance with the invention may be symptomatic or prophylactic treatment. Inflammatory or obstructive airways diseases to which the present invention is applicable include asthma of whatever type or genesis including both intrinsic (non-allergic) asthma and extrinsic (allergic) asthma. Treatment of asthma is also to be understood as embracing treatment of subjects, e.g. of less than 4 or 5 years of age, exhibiting wheezing symptoms and diagnosed or diagnosable as "wheezy infants", an established patient category of major medical concern and now often identified as incipient or early-phase asthmatics. (For convenience this particular asthmatic condition is referred to as "wheezy-infant syndrome".)

Prophylactic efficacy in the treatment of asthma will be evidenced by reduced frequency or severity of symptomatic attack, e.g. of acute asthmatic or bronchoconstrictor attack, improvement in lung function or improved airways hyperreactivity. It may further be evidenced by reduced requirement for other, symptomatic therapy, i.e. therapy for or intended to restrict or abort symptomatic attack when it occurs, for example anti-inflammatory (e.g. corticosteroid) or bronchodilatory. Prophylactic benefit in asthma may in particular be apparent in subjects prone to "morning dipping". "Morning dipping" is a recognised asthmatic syndrome, common to a substantial percentage of asthmatics and characterised by asthma attack, e.g. between the hours of about 4 to 6 am, i.e. at a time normally substantially distant from any previously administered symptomatic asthma therapy.

Other inflammatory or obstructive airways diseases and conditions to which the present invention is applicable include adult/acute respiratory distress syndrome (ARDS), chronic obstructive pulmonary or airways disease (COPD or COAD), including chronic bronchitis, or dyspnea associated therewith, emphysema, as well as exacerbation of airways hyperreactivity consequent to other drug therapy, in particular other inhaled drug therapy. The invention is also applicable to the treatment of bronchitis of whatever type or genesis including, e.g., acute, arachidic, catarrhal, croupus, chronic or phthinoid bronchitis. Further inflammatory or obstructive airways diseases to which the present invention is applicable include pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, asbestosis, chalicosis, ptilosis, siderosis, silicosis, tabacosis and byssinosis.

Having regard to their $\beta_2$ agonist activity, the agents of the invention are also useful in the treatment of a condition requiring relaxation of smooth muscle of the uterus or vascular system. They are thus useful for the prevention or alleviation of premature labour pains in pregnancy. They are also useful in the treatment of chronic and acute urticaria, psoriasis, allergic conjunctivitis, actinitis, hay fever, and mastocytosis.

The agents of the invention are also useful as co-therapeutic agents for use in combination with other drug substances such as anti-inflammatory, bronchodilatory, antihistamine or anti-tussive drug substances, particularly in the treatment of obstructive or inflammatory airways diseases such as those mentioned hereinbefore, for example as potentiators of therapeutic activity of such drugs or as a means of reducing required dosaging or potential side effects of such drugs. An agent of the invention may be mixed with the other drug substance in a fixed pharmaceutical composition or it may be administered separately, before, simultaneously with or after the other drug substance. Accordingly the invention includes a combination of an agent of the invention as hereinbefore described with an anti-inflammatory, bronchodilatory, antihistamine or anti-tussive drug substance, said agent of the invention and said drug substance being in the same or different pharmaceutical composition.

Suitable anti-inflammatory drugs include steroids, in particular glucocorticosteroids such as budesonide, beclamethasone dipropionate, fluticasone propionate, ciclesonide or mometasone furoate, or steroids described in WO 02/88167, WO 02/12266, WO 02/100879, WO 02/00679 (especially those of Examples 3, 11, 14, 17, 19, 26, 34, 37, 39, 51, 60, 67, 72, 73, 90, 99 and 101), WO 03/35668, WO 03/48181, WO 03/62259, WO 03/64445, WO 03/72592, WO 04/39827 and WO 04/66920; non-steroidal glucocorticoid receptor agonists, such as those described in DE 10261874, WO 00/00531, WO 02/10143, WO 03/82280, WO 03/82787, WO 03/86294, WO 03/104195, WO 03/101932, WO 04/05229, WO 04/18429, WO 04/19935 and WO 04/26248; LTB4 antagonists such as BIIL 284, CP-195543, DPC11870, LTB4 ethanolamide, LY 293111, LY 255283, CGS025019C, CP-195543, ONO-4057, SB 209247, SC-53228 and those described in U.S. Pat. No. 5,451,700; LTD4 antagonists such include montelukast, pranlukast, zafirlukast, accolate, SR2640, Wy-48,252, ICI 198615, MK-571, LY-171883, Ro 24-5913 and L-648051; PDE4 inhibitors such cilomilast (Ariflo® GlaxoSmithKline), Roflumilast (Byk Gulden), V-11294A (Napp), BAY19-8004 (Bayer), SCH-351591 (Schering-Plough), Arofylline (Almirall Prodesfarma), PD189659/PD168787 (Parke-Davis), AWD-12-281 (Asta Medica), CDC-801 (Celgene), SelCID™ CC-10004 (Celgene), VM554/UM565 (Vernalis), T-440 (Tanabe), KW-4490 (Kyowa Hakko Kogyo), and those disclosed in WO 92/19594, WO 93/19749, WO 93/19750, WO 93/19751, WO 98/18796, WO 99/16766, WO 01/13953, WO 03/104204, WO 03/104205, WO 03/39544, WO 04/000814, WO 04/000839, WO 04/005258, WO 04/018450, WO 04/018451, WO 04/018457, WO 04/018465, WO 04/018431, WO 04/018449, WO 04/018450, WO 04/018451, WO 04/018457, WO 04/018465, WO 04/019944, WO 04/019945, WO 04/045607 and WO 04/037805; $A_{2A}$ agonists such as those described in EP 1052264, EP 1241176, EP 409595A2, WO 94/17090, WO 96/02543, WO 96/02553, WO 98/28319, WO 99/24449, WO 99/24450, WO 99/24451, WO 99/38877, WO 99/41267, WO 99/67263, WO 99/67264, WO 99/67265, WO 99/67266, WO 00/23457, WO 00/77018, WO 00/78774, WO 01/23399, WO 01/27130, WO 01/27131, WO 01/60835, WO 01/94368, WO 02/00676, WO 02/22630, WO 02/96462, and WO 03/086408; and $A_{2B}$ antagonists such as those described in WO 02/42298.

Suitable bronchodilatory drugs include anticholinergic or antimuscarinic agents, in particular ipratropium bromide, oxitropium bromide, tiotropium salts and CHF 4226 (Chiesi), and glycopyrrolate, but also those described in EP 424021, U.S. Pat. No. 3,714,357, U.S. Pat. No. 5,171,744, WO 01/04118, WO 02/00652, WO 02/51841, WO 02/53564, WO 03/00840, WO 03/33495, WO 03/53966, WO 03/87094, WO 04/018422 and WO 04/05285.

Suitable dual acting bronchodilatory drugs include dual beta-2 adrenoceptor agonist/muscarinic antagonists such as those disclosed in US 2004/0.167167, WO 04/74246 and WO 04/74812.

Suitable antihistamine drug substances include cetirizine hydrochloride, acetaminophen, clemastine fumarate, promethazine, loratidine, desloratidine, diphenhydramine and fexofenadine hydrochloride, activastine, astemizole, azelastine, ebastine, epinastine, mizolastine and tefenadine as well as those disclosed in JP 2004107299, WO 03/099807 and WO 04/026841.

The agents of the invention are also useful as co-therapeutic agents for use in combination other beta-2 adrenoceptor agonists, for example as a rescue medication. Suitable beta-2 adrenoceptor agonists include albuterol (salbutamol), metaproterenol, terbutaline, salmeterol, fenoterol, carmoterol, procaterol, and especially, formoterol and pharmaceutically acceptable salts thereof, and compounds (in free or salt or solvate form) of formula I of WO 0075114, which document is incorporated herein by reference, preferably compounds of the Examples thereof, especially a compound of formula

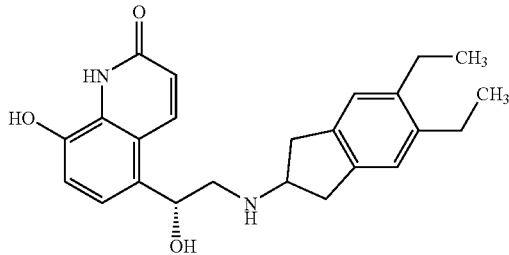

and pharmaceutically acceptable salts thereof, as well as compounds (in free or salt or solvate form) of formula I of WO 04/16601, and also compounds of EP 1440966, JP 05025045, WO 93/18007, WO 99/64035, US 2002/0055651, WO 01/42193, WO 01/83462, WO 02/66422, WO 02/70490, WO 02/76933, WO 03/24439, WO 03/42160, WO 03/42164, WO 03/72539, WO 03/91204, WO 03/99764, WO 04/16578, WO 04/22547, WO 04/32921, WO 04/33412, WO 04/37768, WO 04/37773, WO 04/37807, WO 04/39762, WO 04/39766, WO 04/45618 WO 04/46083, WO 04/80964, EP1460064, WO 04/087142, WO 04/089892, EP 01477167, US 2004/0242622, US 2004/0229904, WO 04/108675, WO 04/108676, WO 05/033121, WO 05/040103 and WO 05/044787.

Other useful combinations of agents of the invention with anti-inflammatory drugs are those with antagonists of chemokine receptors, e.g. CCR-1, CCR-2, CCR-3, CCR-4, CCR-5, CCR-6, CCR-7, CCR-8, CCR-9 and CCR10, CXCR1, CXCR2, CXCR3, CXCR4, CXCR5, particularly CCR-5 antagonists such as Schering-Plough antagonists SC-351125, SCH-55700 and SCH-D, Takeda antagonists such as N-[[4-[[[6,7-dihydro-2-(4-methylphenyl)-5H-benzocyclohepten-8-yl]carbonyl]amino]phenyl]-methyl]tetrahydro-N,N-dimethyl-2H-pyran-4-amin-ium chloride (TAK-770), and CCR-5 antagonists described in U.S. Pat. No. 6,166,037 (particularly claims 18 and 19), WO 00/66558 (particularly claim 8), WO 00/66559 (particularly claim 9), WO 04/018425 and WO 04/026873.

Combinations of agents of the invention and steroids, PDE4 inhibitors, $A_{2A}$ agonists, $A_{2B}$ agonists or LTD4 antagonists may be used, for example, in the treatment of COPD or, particularly, asthma. Combinations of agents of the invention and anticholinergic or antimuscarinic agents, PDE4 inhibitors, $A_{2A}$ agonists, $A_{2B}$ agonists, dopamine receptor agonists or LTB4 antagonists may be used, for example, in the treatment of asthma or, particularly, COPD.

In accordance with the foregoing, the present invention also provides a method for the treatment of an obstructive or inflammatory airways disease which comprises administering to a subject, particularly a human subject, in need thereof a compound of formula I, or a pharmaceutically acceptable salt or solvate thereof, as hereinbefore described. In another aspect, the invention provides a compound of formula I, or a pharmaceutically acceptable salt or solvate thereof, as hereinbefore described for use in the preparation of a medicament for the treatment of an obstructive or inflammatory airways disease.

The agents of the invention may be administered by any appropriate route, e.g. orally, for example in the form of a tablet or capsule; parenterally, for example intravenously; topically to the skin, for example in the treatment of psoriasis; intranasally, for example in the treatment of hay fever; or, preferably, by inhalation, particularly in the treatment of obstructive or inflammatory airways diseases.

In a further aspect, the invention also provides a pharmaceutical composition comprising a compound of formula I in free form or in the form of a pharmaceutically acceptable salt or solvate thereof, optionally together with a pharmaceutically acceptable diluent or carrier therefor. Such compositions may be prepared using conventional diluents or excipients and techniques known in the galenic art. Thus oral dosage forms may include tablets and capsules. Formulations for topical administration may take the form of creams, ointments, gels or transdermal delivery systems, e.g. patches. Compositions for inhalation may comprise aerosol or other atomizable formulations or dry powder formulations.

When the composition comprises an aerosol formulation, it preferably contains, for example, a hydro-fluoro-alkane (HFA) propellant such as HFA134a or HFA227 or a mixture of these, and may contain one or more co-solvents known in the art such as ethanol (up to 20% by weight), and/or one or more surfactants such as oleic acid or sorbitan trioleate, and/or one or more bulking agents such as lactose. When the composition comprises a dry powder formulation, it preferably contains, for example, the compound of formula I having a particle diameter up to 10 microns, optionally together with a diluent or carrier, such as lactose, of the desired particle size distribution and a compound that helps to protect against product performance deterioration due to moisture, such as magnesium stearate, e.g. 0.01 to 1.5%. When the composition comprises a nebulised formulation, it preferably contains, for example, the compound of formula I either dissolved, or suspended, in a vehicle containing water, a co-solvent such as ethanol or propylene glycol and a stabiliser, which may be a surfactant.

The invention also includes (A) a compound of formula I as hereinbefore described in free form, or a pharmaceutically acceptable salt or solvate thereof, in inhalable form; (B) an inhalable medicament comprising such a compound in inhalable form together with a pharmaceutically acceptable carrier in inhalable form; (C) a pharmaceutical product comprising such a compound in inhalable form in association with an inhalation device; and (D) an inhalation device containing such a compound in inhalable form.

Dosages employed in practising the invention will of course vary depending, for example, on the particular condition to be treated, the effect desired and the mode of administration. In general, suitable daily dosages for administration by inhalation are of the order of from 1 to 5000 µg.

The invention is illustrated by the following Examples.

EXAMPLES

Especially preferred compounds of formula I are also compounds of formula XI

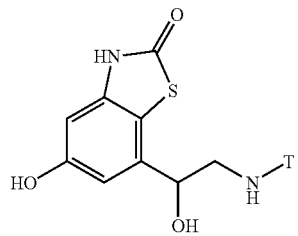

XI wherein T is as shown in the following table, the method of preparation being described hereinafter. All compounds are salts or in the free form. 1H NMR spectra are recorded at 400 MHz in CDCl$_3$ unless otherwise noted. Mass spectra are obtained under electrospray ionisation conditions with LC gradient elution of 5% to 95% acetonitrile-water in the presence of 0.1% formic acid.

| Ex. | T | MS [MH]$^+$ |
|---|---|---|
| 1 | 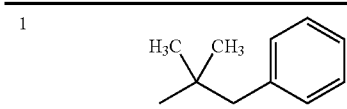 | 359.26 |
| 2 | 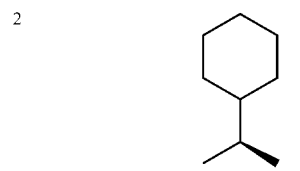 | 337.21 |
| 3 | 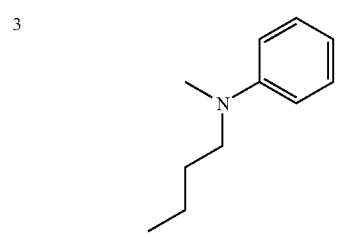 | 374.27 |
| 4 | 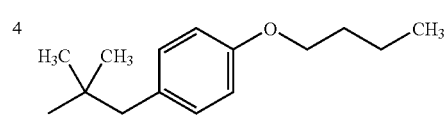 | 431.15 |
| 5 | 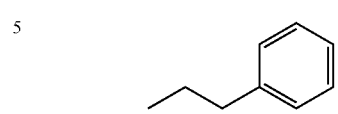 | 331.04 |
| 6 | 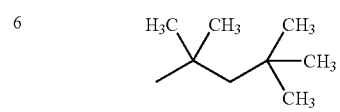 | 339.09 |
| 7 | 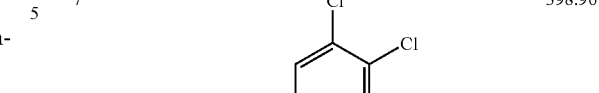 | 398.96 |
| 8 | 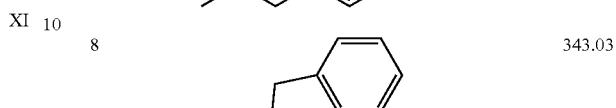 | 343.03 |
| 9 | 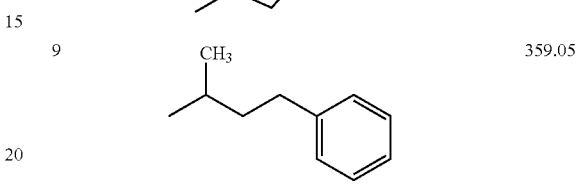 | 359.05 |
| 10 | 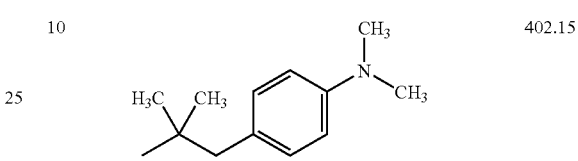 | 402.15 |
| 11 | 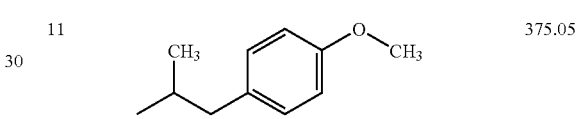 | 375.05 |
| 12 | 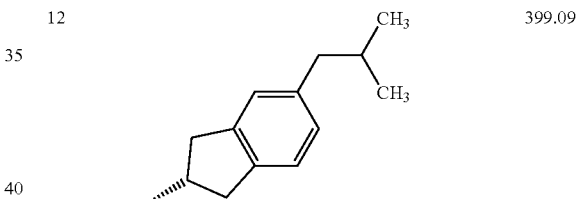 | 399.09 |
| 13 | 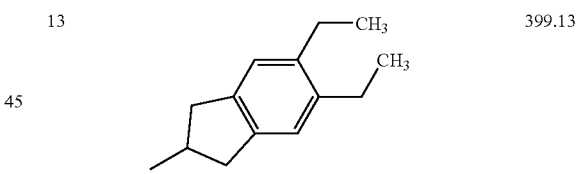 | 399.13 |
| 14 | 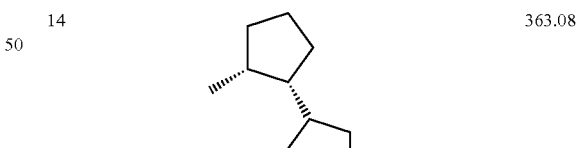 | 363.08 |
| 15 | 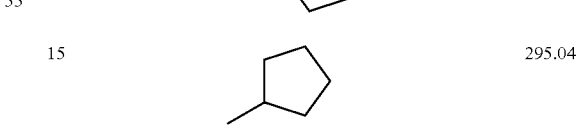 | 295.04 |
| 16 | 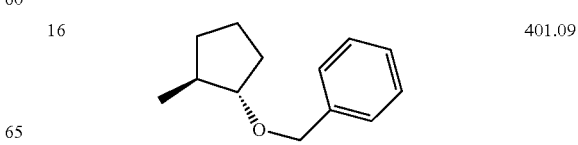 | 401.09 |

| Ex. | T | MS [MH]+ |
|---|---|---|
| 17 | [cyclopentyl-O-CH2-phenyl structure] | 401.05 |
| 18 | [H3C-C(CH3)2-CH2-phenyl-N(CH3)2 structure] | 402.15 |

PREPARATION OF INTERMEDIATES

Abbreviations used are as follows: DCM is dichloromethane, DMF is dimethylformamide, and DMSO is dimethylsulphoxide, THF is tetrahydrofuran.

1-Bromo-3-tert-butoxy-5-fluorobenzene tert-Butanol (28.2 g) is dissolved in dimethyl acetamide (200 ml). NaH (15.6 g, 60% dispersion in oil) is added over 15 minutes. The reaction mixture is stirred at room temperature for 2 hours. 3,5-difluorobromobenzene (50 g) is added drop wise over 30 minutes. The reaction mixture is stirred at room temperature until shown to be complete by HPLC. The reastion mixture is quenched by addition of water (10 ml), washed with water (1×), dried over MgSO$_4$, filtered and the solvent removed in vacuo to give the title compound. $^1$H nmr (CDCl$_3$, 400 MHz); 7.00 (ddd, 1H), 6.95 (dd, 1H), 6.68 (ddd, 1H), 1.4 (s, 9H).

3-tert-Butoxy-5-fluoro-phenylamine

1-Bromo-3-tert-butoxy-5-fluorobenzene (56.1 g), benzophenone (50.9 g), NaOMe (50.5 g) and 2,2'-Bis-diphenylphosphanyl-[1,1']binaphthalenyl (17.5 g) are dissolved in toluene (500 ml). The reaction mixture is flushed with argon, Pd$_2$(dba)$_3$ (5.4 g) is added and the reaction mixture is heated to 80° C. for 40 hours. The reaction mixture is quenched with water. The organics are separated, dried over MgSO$_4$, filtered and the solvent removed in vacuo. The intermediate is obtained by flash column chromatography (silica, eluent dichloromethane). The resulting product is then dissolved in MeOH (1 L). NaOAc (46.1 g), hydroxylamine hydrochloride (29.1 g) are added and the reaction mixture is stirred at room temperature for 2.5 hours. The reaction mixture is quenched with 0.1M NaOH, extracted into DCM (2×), dried over MgSO$_4$, filtered and the solvent removed in vacuo to give the title compound. $^1$H nmr (CDCl$_3$, 400 MHz); 6.20 (m, 3H), 3.75 (br s, 2H), 1.4 (s, 9H).

1-tert-Butoxy-3-fluoro-5-isothiocyanatobenzene

Thiophosgene (33.6 g) in CHCl$_3$ (250 ml) and K$_2$CO$_3$ (64.7 g) in H$_2$O (450 ml) are added, separately and simultaneously, drop wise to a solution of 3-tert-Butoxy-5-fluoro-phenylamine (42.9 g) in CHCl$_3$ (350 ml) at 0° C. The reaction mixture is warmed to room temperature over night. The organics are separated and washed with water (3×), brine (1×), dried over MgSO$_4$ and the solvent removed in vacuo. The title compound is obtained by flash column chromatography (silica, eluent dichloromethane/iso-hexane 1:3). $^1$H nmr (CDCl$_3$, 400 MHz); 6.70 (m, 3H), 1.40 (s, 9H).

(3-tert-Butoxy-5-fluoro-phenyl)-thiocarbamic acid O-isopropyl ester 1-tert-Butoxy-3-fluoro-5-isothiocyanato-benzene (24.0 g) and triethylamine (10.9 g) are dissolved in iso-propanol (150 ml). The reaction mixture is refluxed for 18 hours and the solvent is removed by vacuo. The crude product is dissolved in hexane:diethyl ether (19:1). The diethyl ether is removed by vacuo and the solution is cooled to 0° C. for 3 hours. The solution is filtered to give the title compound. 1H nmr (CDCl$_3$, 400 MHz); 8.10 (br s, 1H), 6.65 (br s, 2H), 6.45 (ddd, 1H) 5.60 (sept, 1H), 1.35 (d, 6H), 1.30 (s, 9H).

5-tert-Butoxy-2-isopropoxy-benzothiazole-7-carbaldehyde (3-tert-Butoxy-5-fluoro-phenyl)-thiocarbamic acid O-isopropyl ester (2.2 g) is dissolved in dry tetrahydrofuran (20 ml) The reaction mixture is cooled to −78° C. and tert-butyl lithium (15.2 ml, of 1.5 M solution) is added over 20 minutes. The reaction mixture is then warmed to −10° C. for 75 minutes. The reaction mixture is then re-cooled to −78° C., N,N-dimethylformamide (1.5 g) is added and the reaction mixture is slowly warmed to room temperature then stirred at −10° C. for 1 hour. The reaction mixture is quenched with HCl$_{(aq)}$ (5 ml, of a 2 M solution), the organics are separated between ethyl acetate/water and removed in vacuo. The title compound is obtained by flash column chromatography (silica, eluent ethyl acetate/iso-hexane 1:9). MS (ES+) m/e 294 (MH$^+$) LCT50865

5-tert-Butoxy-2-isopropoxy-7-vinylbenzothiazole

Ph$_3$PMe.Br (5.0 g) is dissolved in dry tetrahydrofuran (100 ml) under argon. N-butyl lithium (8.8 ml, of 1.6 M solution) is added at room temperature over 10 minutes and reaction mixture stirred for a further 30 minutes. A solution of 5-tert-Butoxy-2-isopropoxy-benzothiazole-7-carbaldehyde (1.25 g) in dichloromethane (40 ml) is added drop wise to the reaction mixture and the reaction mixture is stirred for 4.5 hours at room temperature. The solvent is removed in vacuo, redissolved in ethyl acetate, washed with water (3×), brine (1×), dried over MgSO$_4$, filtered and the solvent removed in vacuo. The title compound is obtained by flash column chromatography (silica, eluent ethyl acetate/iso-hexane 1:9). MS (ES+) m/e 292 (MH$^+$) LCT55980

(R)-1-(5-tert-Butoxy-2-isopropoxy-benzothiazol-7-yl)-ethane-1,2-diol

K$_3$Fe(CN)$_6$ (1.2 g), K$_2$CO$_3$ (0.5 g), (DHQD)$_2$PHAL (19 mg) are dissolved in tert-butanol/water (15 ml, 1:1 mix) under argon and stirred for 15 minutes. The reaction mixture is cooled to 0° C. and OSO$_4$ (3.1 mg) is added followed by 5-tert-Butoxy-2-isopropoxy-7-vinyl-benzothiazole (0.35 g). The reaction mixture is stirred over night at room temperature. The reaction mixture is quenched with sodium-metabisulphate (1 g) and stirred for 1.5 hours. Ethyl acetate is added, the organics are separated, washed with (2×) water, (1×) brine, dried over MgSO$_4$, filtered and the solvent removed in vacuo. The title compound is obtained by flash column chromatography (silica, eluent ethyl acetate/iso-hexane 2:5). MS (ES+) m/e 326 (MH$^+$) LCT56091

Methanesulfonic acid (R)-2-(5-tert-butoxy-2-isopropoxy-benzothiazol-7-yl)-2-hydroxy-ethyl ester Methane sulfonylchloride (35 mg) is added to a solution of (R)-1-(5-tert-Butoxy-2-isopropoxy-benzothiazol-7-yl)-ethane-1,2-diol (100 mg) in pyridine (2 ml) at 0° C. The reaction mixture is then stirred at 0° C. for 3.5 hours. The solvent is removed in vacuo, The resulting residue is partitioned between $HCl_{(aq)}$ (2M) and ether. The organics is washed with water (1×), brine (1×), dried over $MgSO_4$, filtered and the solvent removed in vacuo to give the title compound. $^1H$ nmr ($CDCl_3$, 400 MHz); 7.20 (d, 1H), 6.80 (d, 1H), 5.30 (sept, 1H), 5.10 (t, 1H), 4.30 (d, 2H), 3.00 (s, 3H), 1.40 (d, 6H), 1.30 (s, 9H).

(S)-1-(5-tert-Butoxy-2-isopropoxy-benzothiazol-7-yl)-ethane-1,2-diol $K_3Fe(CN)_6$ (3.4 g), $K_2CO_3$ (1.4 g), $(DHQ)_2PHAL$ (53 mg) in tert-butanol/water (40 ml, 1:1 mix) under argon is stirred for 20 minutes. The reaction mixture is cooled to 0° C. and $OsO_4$ (8.6 mg) is added followed by 5-tert-Butoxy-2-isopropoxy-7-vinyl-benzothiazole (1.0 g). The reaction mixture is stirred over night at room temperature. The reaction mixture is quenched with sodium-metabisulfate (1.2 g) and stirred for 1.5 hours. Ethyl acetate is added, the organics are separated, washed with (2×) water, (1×) brine, dried over $MgSO_4$, filtered and the solvent removed in vacuo. The title compound is obtained by flash column chromatography (silica, eluent ethyl acetate/iso-hexane 1:3). MS (ES+) m/e 326.12 LCT60289

Methanesulfonic acid (S)-2-(5-tert-butoxy-2-isopropoxy-benzothiazol-7-yl)-2-hydroxy-ethyl ester Methane sulfonylchloride (112 mg) is added to (S)-1-(5-tert-Butoxy-2-isopropoxy-benzothiazol-7-yl)-ethane-1,2-diol (289 mg) in pyridine (2 ml) at 0° C. The reaction mixture is then stirred at 0° C. for 3 hours. The solvent is removed in vacuo, The resulting residue is partitioned between $HCl_{(aq)}$ (2M) and ether. The organics is washed with water (2×), brine (1×), dried over $MgSO_4$, filtered and the solvent removed in vacuo to give the title compound. $^1H$ nmr ($CDCl_3$, 400 MHz); 7.20 (d, 1H), 6.80 (d, 1H), 5.30 (sept, 1H), 5.10 (t, 1H), 4.30 (d, 2H), 3.00 (s, 3H), 1.40 (d, 6H), 1.30 (s, 9H).

2-(4-Butoxy-phenyl)-1,1-dimethyl-ethylamine

This compound is prepared following the procedure described in international patent application WO 01/83462 MS (ES+) m/e 222.20 (MH+) 20% LCT59933

[4-(2-Amino-2-methyl-propyl)-phenyl]-dimethylamine

This compound is prepared following the procedure described in international patent application WO 01/83462 MS (ES+) m/e 193 (MH+) 2% LCT59932

(S)-5-Isobutyl-indan-2-ylamine (a) (S)-5-Bromo-indan-2-ylamine

This compound is prepared following the procedures described in international patent application WO 96/23760.

(b) (S)-(5-Isobutyl-indan-2-yl)-carbamic acid benzyl ester (S)-5-Bromo-indan-2-ylamine (1.0 g) suspended in dichloromethane (10 ml) is cooled to 0° C. and benzyl chloroformate (0.74 ml) is added dropwise and the reaction mixture is stirred for 0.5 hour. The solution is filtered to give (S)-(5-Bromo-indan-2-yl)-carbamic acid benzyl ester. $PdCl_2(dppf)_2$ (59 mg) is placed in a dry flask under argon and isobutyl zinc bromide (50 ml, 0.5 M solution in THF) is added. (5-Bromo-indan-2-yl)-carbamic acid benzyl ester (2.50 g) is dissolved in dry THF (2 ml) and the solution is added to the reaction mixture. The reaction mixture is stirred at 50° C. for 18 hours then quenched with $HCl_{(aq)}$ (2M) and partitioned between ethyl acetate and water. The organic layer is dried over $MgSO_4$, filtered and the solvent removed in vacuo. The title compound is obtained by flash column chromatography (silica, eluent ethyl acetate/iso-hexane 1:4). $^1H$ nmr ($CDCl_3$, 400 MHz); 7.35 (m, 5H), 7.10 (d, 1H), 7.00 (s, 1H), 6.90 (d, 1H), 5.1 (s, 2H), 4.55 (m, 1H), 3.30 (m, 2H), 2.75 (dt, 2H), 2.45 (d, 2H), 1.80 (m, 1H), 0.90 (d, 6H).

(c) (S)-5-Isobutyl-indan-2-ylamine (S)-(5-Isobutyl-indan-2-yl)-carbamic acid benzyl ester ( ) is dissolved in methanol (100 ml), 10% Pd—C (200 mg) is added and the flask is purged with $H_{2(g)}$ (0.35 bar). The reaction mixture is stirred for 18 hours, the catalyst is filtered off. The solvent is removed in vacuo to give title compound. $^1H$ nmr ($CDCl_3$, 400 MHz); 7.10 (d, 1H), 7.00 (s, 1H), 6.90 (d, 1H), 3.85 (m, 1H), 3.15 (dd, 2H), 2.65 (dt, 2H), 2.45 (d, 2H), 1.80 (br m, 3H), 0.90 (d, 6H).

5,6-Diethyl-indan-2-ylamine

This compound is prepared following the procedure described in international patent application WO 03/76387.

(R,R)-Bicyclopentyl-2-ylamine

This compound is prepared from Bicyclopentyl-2-one by the procedure of S. Hartmann et al *Eur. J. Med. Chem.* (2000), 35, 377-392. MS (ES+) m/e 154.23 (MH+) LCT59419

Example 1

(R)-7-[2-(1,1-Dimethyl-2-phenyl-ethylamino)-1-hydroxy-ethyl]-5-hydroxy-3H-benzothiazol-2-one a) (R)-1-(5-tert-Butoxy-2-isopropoxy-benzothiazol-7-yl)-2-(1,1-dimethyl-2-phenyl-ethylamino)-ethanol Methanesulfonic acid (R)-2-(S-tert-butoxy-2-isopropoxy-benzothiazol-7-yl)-2-hydroxy-ethyl ester (122 mg) and phentermine (165 mg) are dissolved in toluene (2 ml). The reaction mixture is heated to 90° C. for 20 hours. The solvent is removed in vacuo and (R)-1-(5-tert-Butoxy-2-isopropoxy-benzothiazol-7-yl)-2-(1,1-dimethyl-2-phenyl-ethylamino)-ethanol is obtained by reversed phase column chromatography using a Jones Flashmaster Personal™ flash chromatography system (ISOLUTE FLASH C18, gradient elution AcCN/water 0 to 60%). MS (ES+) m/e 457.32 (MH+) LCT56716 b) (R)-7-[2-(1,1-Dimethyl-2-phenyl-ethylamino)-1-hydroxy-ethyl]-5-hydroxy-3H-benzothiazol-2-one (R)-1-(5-tert-Butoxy-2-isopropoxy-benzothiazol-7-yl)-2-(1,1-dimethyl-2-phenyl-ethylamino)-ethanol (40 mg) is stirred in formic acid (2 ml) for 72 hours. The formic acid is removed in vacuo and the title compound is obtained by reversed phase column chromatography using a Jones Flashmaster Personal™ flash chromatography system (ISOLUTE FLASH C18, gradient elution AcCN/water 0 to 50%). MS (ES+) m/e 359.26 (MH+) LCT57144

Examples 2 to 17

The compounds of Examples 2 to 17 are made using procedures that are analogous to that used in Example 1.

Example 18

(S)-7-{2-[2-(4-Dimethylamino-phenyl)-1,1-dimethyl-ethylamino]-1-hydroxy-ethyl}-5-hydroxy-3H-benzothiazol-2-one a) (S)-1-(5-tert-Butoxy-2-isopropoxy-benzothiazol-7-yl)-2-[2-(4-dimethylamino-phenyl)-1,1-dimethyl-ethylamino]-ethanol

[4-(2-Amino-2-methyl-propyl)-phenyl]-dimethyl-amine (210 mg) and Methanesulfonic acid (S)-2-(5-tert-butoxy-2-isopropoxy-benzothiazol-7-yl)-2-hydroxy-ethyl ester (120 mg) are dissolved in toluene (2 ml). The reaction mixture is heated to 80° C. for 20 hours. The solvent is removed by vacuo to give (S)-1-(5-tert-Butoxy-2-isopropoxy-benzothiazol-7-yl)-2-[2-(4-dimethylamino-phenyl)-1,1-dimethyl-ethylamino]-ethanol. MS (ES+) m/e. 500 b) (S)-7-{2-[2-(4-Dimethylamino-phenyl)-1,1-dimethyl-ethylamino]-1-hydroxy-ethyl}-5-hydroxy-3H-benzothiazol-2-one (S)-1-(5-tert-butoxy-2-isopropoxy-benzothiazol-7-yl)-2-(1,1-dimethyl-2-phenyl-ethylamino)-ethanol (40 mg) is stirred in formic acid (2 ml) for 72 hours. The formic acid is removed by vacuo and the title compound is obtained by reversed phase flash column chromatography using a Jones Flashmaster Personal™ flash chromatography system (ISOLUTE FLASH C18, AcCN/water 0 to 50%). MS (ES+) m/e. 402.15

The invention claimed is:

1. A compound of formula XI

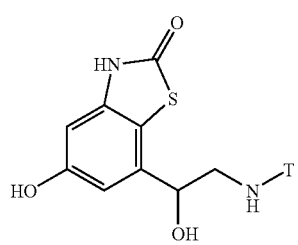

XI in free or salt form, wherein T is selected from the group consisting of:

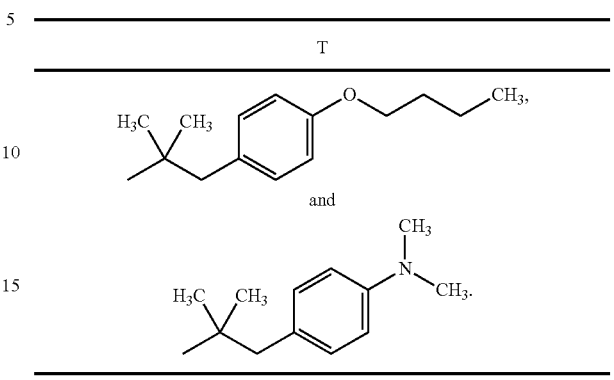

and

2. A compound according to claim 1 in free form.

3. A compound according to claim 1 in salt form.

4. A pharmaceutical composition comprising a compound according to claim 1 together with a pharmaceutically acceptable carrier.

5. A compound of formula XI

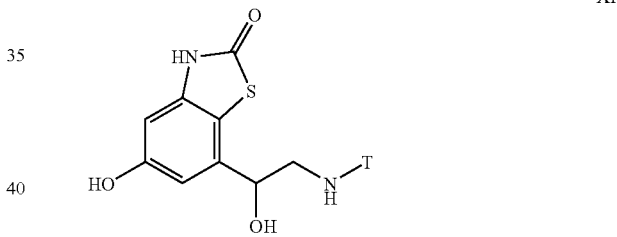

XI in free or salt form, wherein T is

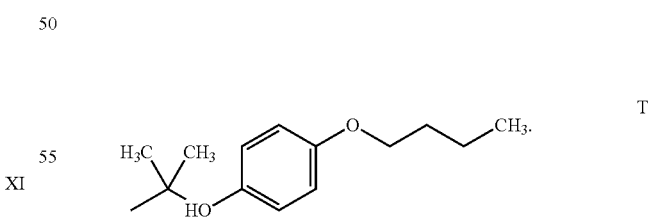

T

6. A compound according to claim 5 in free form.

7. A compound according to claim 5 in salt form.

8. A pharmaceutical composition comprising a compound according to claim 5 together with a pharmaceutically acceptable carrier.

9. A process for the preparation of a compound of formula XI as claimed in claim 5 in free or salt form comprising:

(i) (A) reacting a compound of formula II

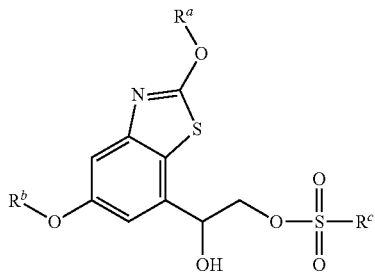

where $R^a$ and $R^b$ are protecting groups and $R^c$ is $C_1$-$C_4$-alkyl or $C_6$-$C_{10}$-aryl, with a compound of formula III $$H_2N\text{-}T \quad \text{III}$$

where T is as defined in claim 5; or (B) reacting a compound of formula IIA

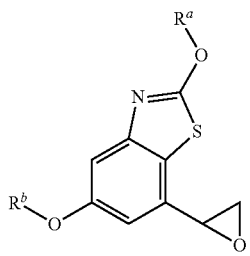

where $R^a$ and $R^b$ are protecting groups, with a compound of formula III, where T is as defined in claim 5;

(ii) removing the protecting groups; and (iii) recovering the resultant compound of formula XI in free or salt form.

10. A process for the preparation of a compound of formula XI as claimed in claim 1 in free or salt form comprising:

(i) (A) reacting a compound of formula II

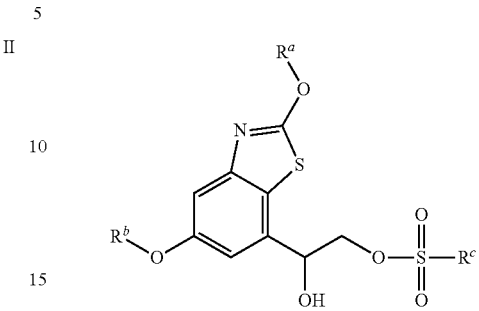

where $R^a$ and $R^b$ are protecting groups and $R^c$ is $C_1$-$C_4$-alkyl or $C_6$-$C_{10}$-aryl, with a compound of formula III $$H_2N\text{-}T \quad \text{III}$$

where T is as defined in claim 1; or (B) reacting a compound of formula IIA

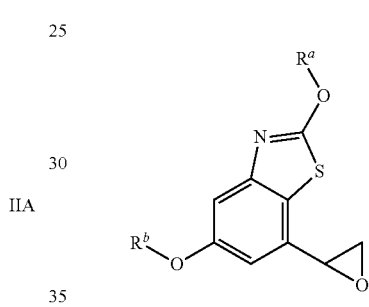

where $R^a$ and $R^b$ are protecting groups, with a compound of formula III, where T is as defined in claim 1;

(ii) removing the protecting groups; and (iii) recovering the resultant compound of formula XI in free or salt form.

11. A method of treating an obstructive or inflammatory airways disease in a subject in need of such treatment, which comprises administering to said subject an effective amount of a compound of formula XI according to claim 1 in free or salt form.

12. A method of treating an obstructive or inflammatory airways disease in a subject in need of such treatment, which comprises administering to said subject an effective amount of a compound of formula XI according to claim 5 in free or salt form.

* * * * *

UNITED STATES PATENT AND TRADEMARK OFFICE
CERTIFICATE OF CORRECTION

PATENT NO. : 8,076,489 B2  Page 1 of 1
APPLICATION NO. : 11/718829
DATED : December 13, 2011
INVENTOR(S) : Robin A Fairhurst et al.

It is certified that error appears in the above-identified patent and that said Letters Patent is hereby corrected as shown below:

In claim 5, line 50-60, column 2, the structure of T should read as follows:

T

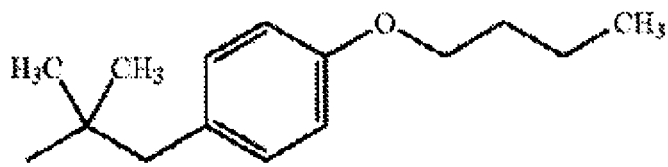

Signed and Sealed this
Sixteenth Day of October, 2012

David J. Kappos
*Director of the United States Patent and Trademark Office*